United States Patent [19]

Liakumovich et al.

[11] 4,232,182
[45] Nov. 4, 1980

[54] PROCESS FOR PURIFYING ISOPRENE

[76] Inventors: Alexandr G. Liakumovich, prospekt Lenina, 23, Kv. 4; Boris I. Pantukh, ulitsa Khudaiberdine, 162, kv. 89, both of Sterlitamak; Tatyana M. Lesteva, 4 Sovetskaya ulitsa, 3a, kv. 12, Leningrad, all of U.S.S.R.

[21] Appl. No.: 853,816

[22] Filed: Nov. 21, 1977

Related U.S. Application Data

[63] Continuation of Ser. No. 764,645, Feb. 1, 1977, abandoned, which is a continuation of Ser. No. 682,105, Apr. 30, 1976, abandoned, which is a continuation of Ser. No. 570,994, Apr. 22, 1975, abandoned.

[51] Int. Cl.$^3$ .................... C07C 7/04; C07C 7/12; C07C 11/18
[52] U.S. Cl. .................... 585/820; 585/821; 585/627
[58] Field of Search .................... 260/681.5, 681; 585/810, 820

[56] References Cited

U.S. PATENT DOCUMENTS

| | | | |
|---|---|---|---|
| 3,409,691 | 1/1968 | Small | 260/681.5 R |
| 3,560,586 | 2/1971 | Kronig et al. | 260/681 |
| 3,804,911 | 4/1974 | Liakumovich et al. | 260/666 A |
| 3,832,416 | 8/1974 | Van Grinsveu | 260/681.5 R |
| 3,972,955 | 8/1976 | Halcour et al. | 260/681 |

Primary Examiner—Veronica O'Keefe
Attorney, Agent, or Firm—Holman & Stern

[57] ABSTRACT

A process for purifying isoprene produced by catalytic decomposition of dimethyldioxane from carbonyl compounds and cyclopentadiene which involves passing isoprene at a temperature of 40° to 70° C. through a bed of a solid product such as an anion exchange resin or alkali (the latter may be used with or without an inert carrier), followed by subjecting the isoprene to close fractionation performed with at least 50 theoretical plates and at a reflux ratio of at least 3. The process of the present invention enables practically complete purification of isoprene from carbonyl compounds and cyclopentadiene. The purified isoprene, when used as a monomer in the production of stereospecific isoprene rubber, results in high-quality products; and reduces by a factor of 2-3 the Ziegler catalyst consumption in the isoprene rubber synthesis.

6 Claims, No Drawings

PROCESS FOR PURIFYING ISOPRENE

This is a continuation of application Ser. No. 764,645, filed Feb. 1, 1977, now abandoned which in turn is continuation of Ser. No. 682,105, filed Apr. 30, 1976 which in turn is continuation of Ser. No. 570,994, filed Apr. 22, 1975, which are now abandoned.

BACKGROUND OF THE INVENTION

1. Field of the Invention

The present invention relates to processes for purifying isoprene produced by catalytic decomposition of dimethyldioxane from carbonyl compounds and cyclopentadiene. The isoprene thus purified is used as a monomer in the production of stereospecific isoprene rubber.

2. Description of the Prior Art

Known in the art is a process for purification of isoprene produced by catalytic decomposition of dimethyldioxane from carbonyl compounds and cyclopentadiene by close fractionation on at least 50 theoretical plates of at least 50 and at a reflux ratio of at least 3, followed by washing the resulting isoprene with water. The residual content of carbonyl compounds and cyclopentadiene in the purified isoprene produced by this process is 0.0005 and 0.0005–0.0004 wt.% respectively. A disadvantage of this process is the relatively high residual content of micro-impurities (carbonyl compounds and cyclopentadiene) in the purified isoprene, which, in turn, results in an impaired quality of isoprene rubber and increased Ziegler catalyst consumption during the subsequent polymerization of the isoprene.

SUMMARY OF THE INVENTION

It is an object of the present to provide a fractionation process for purifying isoprene produced by catalytic decomposition of dimethyldioxane which makes it possible to purify the isoprene to be substantially completely free from carbonyl compounds and cyclopentadiene.

This and other objects of the present invention are accomplished by a process wherein isoprene produced by catalytic decomposition of dimethyldioxane is passed at a temperature of 40° to 70° C. through a bed of a solid product such as an anion exchange resin or alkali, and then subjected to close fractionation using at least 50 theoretical plates and a reflux ratio of at least 3.

When passing isoprene through a bed of a solid product at the above-mentioned temperatures, microimpurities (carbonyl compounds and cyclopentadiene) are converted into highmolecular products, namely fulvenes and polyesters which are easily separated from isoprene by subsequent close fractionation. Anion exchange resin and alkali act as catalysts in this conversion. The content of carbonyl compounds in isoprene after passing through the bed of said solid products is reduced to 0.0005–0.00008 wt.%, while cyclopentadiene content is reduced to 0.0005–0.0001 wt.%. After the close fractionation, the residual content of carbonyl compounds in the purified isoprene is not more than 0.00005 wt.% and that of cyclopentadiene does not exceed 0.00005 wt.%.

As the anion exchange resin it is advisable to use either a reaction product of chloromethylated copolymer of styrene and divinyl-benzene with trimethylamine or a reaction product of epichlorohydrin with polyethylenepolyamine.

To improve the degree of isoprene purification, it is advisable to use an alkali on an inert carrier. As the inert carrier it is preferred to employ silica gel or corundum.

To purify isoprene as extensively as possible, following close fractionation it is advisable to continuously recycle 20 to 80% by weight of the purified isoprene for intermixing with the unpurified starting material isoprene.

DETAILED DESCRIPTION OF THE PREFERRED EMBODIMENTS

The process for purifying isoprene according to the present invention is performed in the following manner.

Isoprene produced by catalytic decomposition of dimethyldioxane and containing 0.1 to 0.2 wt.% of carbonyl compounds (acetaldehyde, acrolein, acetone, isovaleric aldehyde, and the like) and 0.05 to 0.1 wt.% of cyclopentadiene is heated to a temperature within the range of from 40° to 70° C. and passed through a vertical cylindrical reactor filled with a finely divided solid product, viz. an anion exchange resin or alkali (the latter may be employed with or without an inert carrier.

As the anion exchange resin various basic polymers may be used corresponding to the formula $R_4N^+OH^-$, such as a reaction product of a chloro-methylated copolymer of styrene and divinyl benzene with trimethyleneamine, a reaction product of epichlorohydrin with polyethylenepolyamine, and the like. As the alkali, potassium, sodium or lithium hydroxides may be used. As the inert carrier, alumina gel, silica gel, corundum, pumice, and carborundum may be used.

It is advisable that a space velocity of isoprene passed through the reactor filled with the solid product be maintained within the range of from 0.5 to 2 $hr^{-1}$. From the reactor the isoprene is passed into a close fractionation column. Purified isoprene is discharged from the column top, while high-boiling products of converted microimpurities (fulvenes and polyesters) are discharged from the column bottom.

To perform isoprene purification as extensively as possible, it is advisable that 20 to 80 wt.% of purified isoprene containing only microamounts of axeotrope-forming carbonyl compounds be continuously recycled back to the purification process for mixing with the starting isoprene.

The process of the present invention enables substantially complete purification of isoprene from carbonyl compounds and cyclopentadiene. When thus-purified isoprene is employed as a monomer in the production of stereospecific isoprene rubber, the resulting product is of high quality and the Ziegler catalyst consumption is reduced by 2–3 times.

For a better understanding of the present invention, the following examples illustrating the process of isoprene purification are given hereinbelow.

EXAMPLE 1

Isoprene produced by catalytic decomposition of dimethyldioxane and containing 0.2 wt.% of carbonyl compounds and 0.05 wt.% of cyclopentadiene was heated to 60° C. and passed at the space velocity of 1 $hr.^{-1}$ through a vertical cylindrical reactor filled with solid potassium hydroxide having a particle size of 5 to 30 mm. Isoprene discharged from the reactor contained 0.0005 wt.% of carbonyl compounds and 0.0004 wt.% of cyclopentadiene. From the reactor the isoprene was delivered into a close-fractionation column having 50 theoretical plates, the reflux ratio being equal to 3. Purified isoprene was discharged from the column top. The content of carbonyl compounds in the purified isoprene was 0.00005 wt.% and that of cyclopentadiene was 0.00005 wt.%.

EXAMPLE 2

Isoprene produced by catalytic decomposition of dimethyldioxane and containing 0.15 wt.% of carbonyl compounds and 0.1 wt.% of cyclopentadiene was heated to 50° C. and passed at the space velocity of 1.5 hr.$^{-1}$ through a vertical cylindric reactor filled with a finely divided anion exchange resin (reaction product of chloromethylated copolymer of styrene and divinylbenzene with trimethylamine) having a particle size of 1–3 mm. The content of the carbonyl compounds in the isoprene discharged from the reactor was 0.0003 wt.%, and the cyclopentadiene content in the discharged isoprene was 0.0005 wt.%. From the reactor the isoprene was delivered into a close-fractionation column having 55 theoretical plates and a reflux ratio of 4. Purified isoprene was discharged from the column 20 wt.% of the purified isoprene was continuously recycled for mixing with the starting isoprene fed into the the anion exchange resin filled reactor. In the isoprene thus purified there were practically no microimpurities (carbonyl compounds and cyclopentadiene).

EXAMPLE 3

Isoprene produced by catalytic decomposition of dimethyldioxane and containing 0.1 wt.% of carbonyl compounds and 0.08 wt.% of cyclopentadiene was heated to 40° C. and passed at the space velocity of 2 hr$^{-1}$ through a vertical cylindrical reactor filled with solid sodium hydroxide deposited on corundum having a particle size of 2 to 5 mm. The content of carbonyl compounds in the isoprene discharged from the reactor was 0.00008 wt.% and that of cyclopentadiene was 0.00012 wt.%. From the reactor the isoprene was fed into a close-fractionation column having 60 theoretical plates and a reflux ratio of 3.2. Purified isoprene was discharged from the column top. The content of carbonyl compounds in the thus-purified isoprene was less than 0.00002 wt.% and that of cyclopentadiene was also less than 0.00002 wt.%.

EXAMPLE 4

Isoprene produced by catalytic decomposition of dimethyldioxane and containing 0.15 wt.% of carbonyl compounds and 0.1 wt.% of cyclopentadiene was heated to 70° C. and passed at the space velocity of 0.8 hr$^{-1}$ through a vertical cylindrical reactor filled with potassium hydroxide deposited on silica gel having a particle size of 2 to 5 mm. The content of carbonyl compounds in the isoprene discharged from the reactor was 0.0005 wt.%. The content of cyclopentadiene in the discharged isoprene was 0.0002 wt.%. From the reactor the isoprene was fed into a close-fractionation column having 60 theoretical plates and a reflux ratio of 5. The thus-purified isoprene was discharged from the column top. 80% of the purified isoprene was continuously recycled for mixing with the starting isoprene fed into the reactor filled with potassium hydroxide deposited on said carrier. Isoprene purified by this process contained 0.00005 wt.% of carbonyl compounds and 0.0005 wt.% of cyclopentadiene.

EXAMPLE 5

Isoprene produced by catalytic decomposition of dimethyldioxane and containing 0.2 wt.% of carbonyl compounds and 0.08 wt.% of cyclopentadiene was heated to 65° C. and passed at the space velocity of 2 hr$^{-1}$ through a vertical cylindrical reactor filled with a finely divided anion exchange resin (reaction product of epichlorohydrin and polyethylenepolyamine) having a particle size 1 to 3 mm. The content of carbonyl compounds in the isoprene discharged from the reactor was 0.0004 wt.% and that of cyclopentadiene was 0.0003 wt.%. From the reactor the isoprene was fed into a close-fractionation column having 50 theoretical plates and a reflux ratio of 5. The purified isoprene was discharged from the column top. The purified product contained practically no microimpurities (carbonyl compounds and cyclopentadiene).

What is claimed is:

1. A process for purifying isoprene produced by catalytic decomposition of dimethyldioxane from carbonyl compounds and cyclopentadiene which consists of the steps of passing isoprene at a temperature of from 40° to 70° C. through a bed of a solid product selected from the group consisting of an anion exchange resin and alkali, and subjecting said isoprene to close fractionation on at least 50 theoretical plates and at a reflux ratio of at least 3 recycling 20 to 80 wt.% of said purified isoprene following close fractionation for admixture with the starting isoprene to be purified.

2. A process as claimed in claim 1, wherein said anion exchange resin comprises a reaction product of a chloromethylated copolymer of styrene and divinylbenzene with trimethylamine.

3. A process as claimed in claim 1, wherein said anion exchange resin comprises a reaction product of epichlorohydrin with polyethylenepolyamine.

4. A process as claimed in claim 1, wherein said solid product is an alkali deposited on an inert carrier.

5. A process as claimed in claim 4, wherein said inert carrier is selected from the group consisting of silica gel and corundum.

6. A process as claimed in claim 1 wherein said solid product is an anion exchange resin.

* * * * *